(12) United States Patent
Kim et al.

(10) Patent No.: US 11,909,431 B2
(45) Date of Patent: Feb. 20, 2024

(54) CAPSULE-TYPE ENDOSCOPE CAPABLE OF TWO-WAY COMMUNICATION

(71) Applicant: Industry-Academic Cooperation Foundation, Chosun University, Gwangju (KR)

(72) Inventors: Youn Tae Kim, Daejeon (KR); Jong Jin Baek, Jeollanam-do (KR); Ji Won Park, Gwangju (KR); Min Gu Kang, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 597 days.

(21) Appl. No.: 17/117,956

(22) Filed: Dec. 10, 2020

(65) Prior Publication Data
US 2021/0184712 A1    Jun. 17, 2021

(30) Foreign Application Priority Data
Dec. 11, 2019    (KR) .................. 10-2019-0164955

(51) Int. Cl.
*A61B 1/00*    (2006.01)
*H04B 1/16*    (2006.01)
(Continued)

(52) U.S. Cl.
CPC ....... *H04B 1/1638* (2013.01); *A61B 1/00016* (2013.01); *A61B 1/041* (2013.01); *A61B 90/98* (2016.02); *H04B 13/005* (2013.01)

(58) Field of Classification Search
CPC .. H04B 13/005; H04B 1/1638; H04B 1/1607; A61B 1/00016; A61B 90/98;
(Continued)

(56) References Cited

U.S. PATENT DOCUMENTS

2006/0264702 A1* 11/2006 Ishibashi .................. A61B 1/04
                                                        600/101
2008/0103356 A1*  5/2008 Minai ................ A61B 1/00016
                                                        600/103
(Continued)

FOREIGN PATENT DOCUMENTS

EP         1719446           2/2005
KR    10-2007-0018858        2/2007
(Continued)

OTHER PUBLICATIONS

Office Action dated May 27, 2021 in corresponding Korean Application No. 10-2019-0164955.

*Primary Examiner* — Timothy J Neal
(74) *Attorney, Agent, or Firm* — Renner, Otto, Boisselle & Sklar, LLP (57) ABSTRACT

A capsule-type endoscope capable of two-way communication includes an RFID receiving antenna receiving an RFID signal, a first matching circuit for impedance matching with the RFID receiving antenna, a human body communication electrode comprised of a ground electrode and a signal electrode transmitting a signal for human body communication, and a second matching circuit for impedance matching with the human body communication electrode.

5 Claims, 6 Drawing Sheets

(51) Int. Cl.
*H04B 13/00* (2006.01)
*A61B 90/98* (2016.01)
*A61B 1/04* (2006.01)

(58) Field of Classification Search
CPC ... A61B 5/073; A61B 1/041; A61B 2562/162; A61B 5/6861; A61B 5/686
See application file for complete search history.

(56) References Cited

U.S. PATENT DOCUMENTS

| | | | |
|---|---|---|---|
| 2008/0125623 A1* | 5/2008 | Tamura | A61B 5/0028 |
| | | | 600/101 |
| 2018/0064366 A1* | 3/2018 | Sweeney | A61B 5/073 |
| 2020/0243953 A1* | 7/2020 | Nikolayev | A61B 5/073 |
| 2021/0030305 A1* | 2/2021 | Nikolayev | A61B 5/073 |

FOREIGN PATENT DOCUMENTS

| | | |
|---|---|---|
| KR | 10-1021495 B1 | 3/2011 |
| KR | 101021495 B1 * | 3/2011 |
| KR | 10-1317043 B1 | 10/2013 |
| WO | 2008/065839 A1 | 6/2008 |

* cited by examiner

CAPSULE-TYPE ENDOSCOPE CAPABLE OF TWO-WAY COMMUNICATION

CROSS-REFERENCE TO RELATED APPLICATION(S)

This application claims the benefit under 35 USC 119(a) of Korean Patent Application No. 10-2019-0164955 filed on Dec. 11, 2019 in the Korean Intellectual Property Office, the entire disclosure of which is incorporated herein by reference for all purposes.

BACKGROUND

The present disclosure relates to a capsule-type endoscope capable of two-way communication A capsule-type endoscope is a medical device used to examine internal organs of the body. When a patient swallows the capsule-type endoscope like a pill, the capsule-type endoscope moves from the oral cavity to the rectum, capturing images of internal organs such as the stomach, small intestine, and large intestine, and is then discharged from the body.

The images captured by the camera provided in the capsule-type endoscope are wirelessly transmitted to an image storage device worn by the patient. Images transmitted during the examination period are continuously stored in the image storage device, and after the examination is completed, the doctor diagnoses the patient's health condition using the images stored in the image storage device. There is none of the pain and discomfort associated with general endoscopy, and there is the advantage of obtaining images of the small intestine that cannot be reached with general endoscopy.

On the other hand, due to the physical size and high dielectric constant of the human body, many electromagnetic waves from surrounding sources are induced into the human body. These signals operate as very large interference signals in human body communication, which communicates with the human body as a medium, thereby deteriorating the communication quality of human body communication. Signals received to the human body from the outside are generated at a relatively long distance, and signals measured at two points on the human body, especially two points on the abdomen, may have the same value (magnitude and phase). These interference signals induced by the human body may have common-mode interference signal characteristics and may be eliminated by using a differential receiver structure.

In the case of a capsule-type endoscope, while the battery capacity thereof may be limited, technology is advancing toward obtaining higher and higher levels of resolution and larger amounts of image information. Unlike receivers located outside of the human body, when a differential receiving structure is applied to the capsule-type receiver to remove interference signals induced by the human body, not only the interference signal but also the human body communication signal is canceled due to the limited size of the capsule, making it difficult to apply.

In addition, in a method of directly transmitting a digital signal, the modulation and transmission unit is comprised of a logic circuit and a driving circuit having a high current capacity for driving a load, so that power consumption may be significantly reduced. This structure has the advantage of not requiring a frequency booster and an RF amplifier that require a lot of power to convert to RF. In contrast, a receiving structure for directly receiving a digital signal consumes more power than a transmitter, in a structure for restoring an analog signal into a digital signal and a synchronization circuit and a demodulation circuit for obtaining synchronization from the restored digital signal. With such a characteristic, the human body communication technology applied to the capsule-type endoscope is configured for transmission only, and requires an additional wireless communication technology driven at low power for bidirectional communication.

The latest capsule type endoscope is gradually researched and applied from a simple function of obtaining image information of the digestive tract through peristalsis and to additional functions of performing a stop, movement and simple treatment in the digestive tract. To this end, two-way communication should be established.

The information transmitted from the capsule-type endoscope to the external receiver is image information with a high transmission rate, but the information transmitted from the outside to the inside requires asymmetric communication in which very little information such as wake-up/position control/shooting period control is transmitted. In addition, to achieve this purpose, technology capable of significantly reducing power consumption in consideration of limited battery capacity should be applied.

SUMMARY

According to an exemplary embodiment, a capsule-type endoscope capable of two-way communication is provided.

According to a first embodiment, a capsule-type endoscope capable of two-way communication includes an RFID receiving antenna receiving an RFID signal, a first matching circuit for impedance matching with the RFID receiving antenna, a human body communication electrode comprised of a ground electrode and a signal electrode transmitting a signal for human body communication, and a second matching circuit for impedance matching with the human body communication electrode.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that would be well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will fully convey the scope of the disclosure to one of ordinary skill in the art.

Herein, it is noted that use of the term "may" with respect to an example or embodiment, e.g., as to what an example or embodiment may include or implement, means that at least one example or embodiment exists in which such a feature is included or implemented while all examples and embodiment s are not limited thereto.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there may be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as illustrated in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes illustrated in the drawings may occur. Thus, the examples described herein are not limited to the specific shapes illustrated in the drawings, but include changes in shape that occur during manufacturing.

The features of the examples described herein may be combined in various ways as will be apparent after an understanding of the disclosure of this application. Further, although the examples described herein have a variety of configurations, other configurations are possible as will be apparent after an understanding of the disclosure of this application.

The drawings may not be to scale, and the relative size, proportions, and depiction of elements in the drawings may be exaggerated for clarity, illustration, and convenience.

Hereinafter, embodiment of the present disclosure will be described with reference to the accompanying drawings. However, the embodiment of the present disclosure may be modified into various other forms, and the scope of the present disclosure is not limited to the embodiment of the present disclosures described below. Shapes and sizes of elements in the drawings may be exaggerated for more clarity, and elements indicated by the same reference numerals in the drawings are the same elements.

Figure 1:
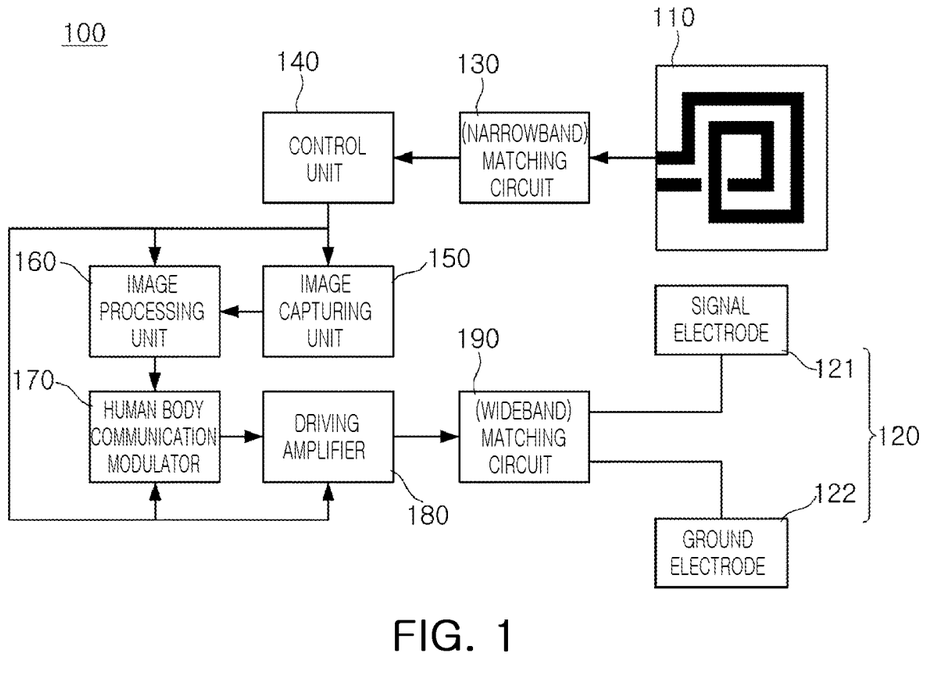
FIG. 1 is an internal block diagram of a capsule-type endoscope according to an embodiment of the present disclosure.

FIG. 1 is an internal block diagram of a capsule-type endoscope 100 according to an embodiment of the present disclosure.

As illustrated in FIG. 1, the capsule-type endoscope 100 according to an embodiment of the present disclosure includes an RFID receiving antenna 110 receiving an RFID signal, a first matching circuit 130 for impedance matching with the RFID receiving antenna 110, a human body communication electrode 120 comprised of a signal electrode 121 and a ground electrode 122, to transmit a signal for human body communication, and a second matching circuit 190 for impedance matching with the human body communication electrode 120, and as other configurations, may include a control unit 140, an image capturing unit 150, an image processing unit 160, a human body communication modulator 170, and a driving amplifier 180.

The RFID receiving antenna 110 may be referred to as a loop antenna, and may receive an RFID signal transmitted from an RFID reader (not illustrated) provided outside of the human body. The received RFID signal may be transmitted to the control unit 140 through the narrowband matching circuit 130 (hereinafter, referred to as a "first matching circuit"). The above-described first matching circuit 130 may be a circuit for impedance matching with the RFID receiving antenna 110.

The RFID technology is comprised of a reader or reader emitting high power and a tag writing information to an integrated circuit from the power radiated from the reader and transmitting the information to the reader through an antenna. The tag is comprised of an antenna and an integrated circuit (an RFID chip), and is classified into one of a passive method in which information on the chip is read and communicated with only the power received from the reader, a semi-passive method in which the power of a reader is used only for communication with the tag's own power consumed in reading information from the chip, and an active method in which the tag's own power is used to read information from the chip and communicate the information. The capsule-type endoscope basically has its own battery, and thus, may be combined with all of the passive, semi-passive, and active technologies used in RFID.

In addition, data to be transmitted from an external transmitter to a capsule-type receiver located in the human body through RFID communication is simple information necessary for control, such as wake-up/position control/direction setting/image capturing cycle or the like and may thus have a relatively very low data transmission rate. Accordingly, even when an active method is adopted, high power is not consumed for recording chip information. When using a passive or semi-passive method, there is an advantage that standby power is not generated.

The RFID reader or the reader is located outside of the human body and is relatively freer as compared the capsule-type endoscope in terms of power consumption. The RFID method using 13.56 MHz has the advantage of transmitting power to a capsule-type endoscope located in the body and performing communication, using a magnetic field that is not affected by the human body. In the case of a receiving antenna used in a tag, a resonance structure is formed using the inductance of the loop antenna and the chip capacitor, a passive element, to be used in various small devices such as wrist watches, key chains, rings and the like. In the case of a loop antenna, the size thereof is determined in consideration of the physical size of the tag, and the impedance required for the operating frequency is implemented through a matching circuit.

On the other hand, the human body communication electrode 120 is comprised of a signal electrode 121 and a ground electrode 122, and may be an electrode transmitting a signal for human body communication through a human body as a medium. Similarly, the wideband matching circuit 190 (hereinafter, referred to as a "second matching circuit") may be a circuit for impedance matching with the human body communication electrode 120 described above.

On the other hand, the operation will be described referring to the block diagram of the capsule-type endoscope 100 according to an embodiment of the present disclosure with reference to FIG. 1. To receive an RFID signal output from an RFID reader (not illustrated) provided outside of the human body, the RFID receiving antenna 110 is combined with a first matching circuit and receives a signal of an RFID frequency band, and transmits a control signal to the control unit 140 through an RFID chip (not illustrated).

On the other hand, the capsule-type endoscope 100, inserted into a digestive organ through the mouth, reaches the stomach through an esophagus at relatively high speed. The capsule-type endoscope 100 that has reached the stomach stays on the stomach for a long time before moving to a small intestine. In this case, a command to adjust the shooting period by grasping the moving state of the capsule-type endoscope 100 may be transmitted to the capsule-type endoscope 100.

This control command is transmitted through the RFID reader outside of the human body, and the transmitted control signal is transmitted to the control unit 140 of the capsule-type endoscope 100 through an RFID chip. The control unit 140 transmits a control signal for data processing to the image capturing unit 150, the image processing unit 160, and the human body communication modulator 170. The data input to the human body communication modulator 170 through the image processing unit 160 may be transmitted through the signal electrode 121 after obtaining sufficient current (or voltage) that may be transmitted through the human body as a load, through the driving amplifier 180.

Figure 2A:
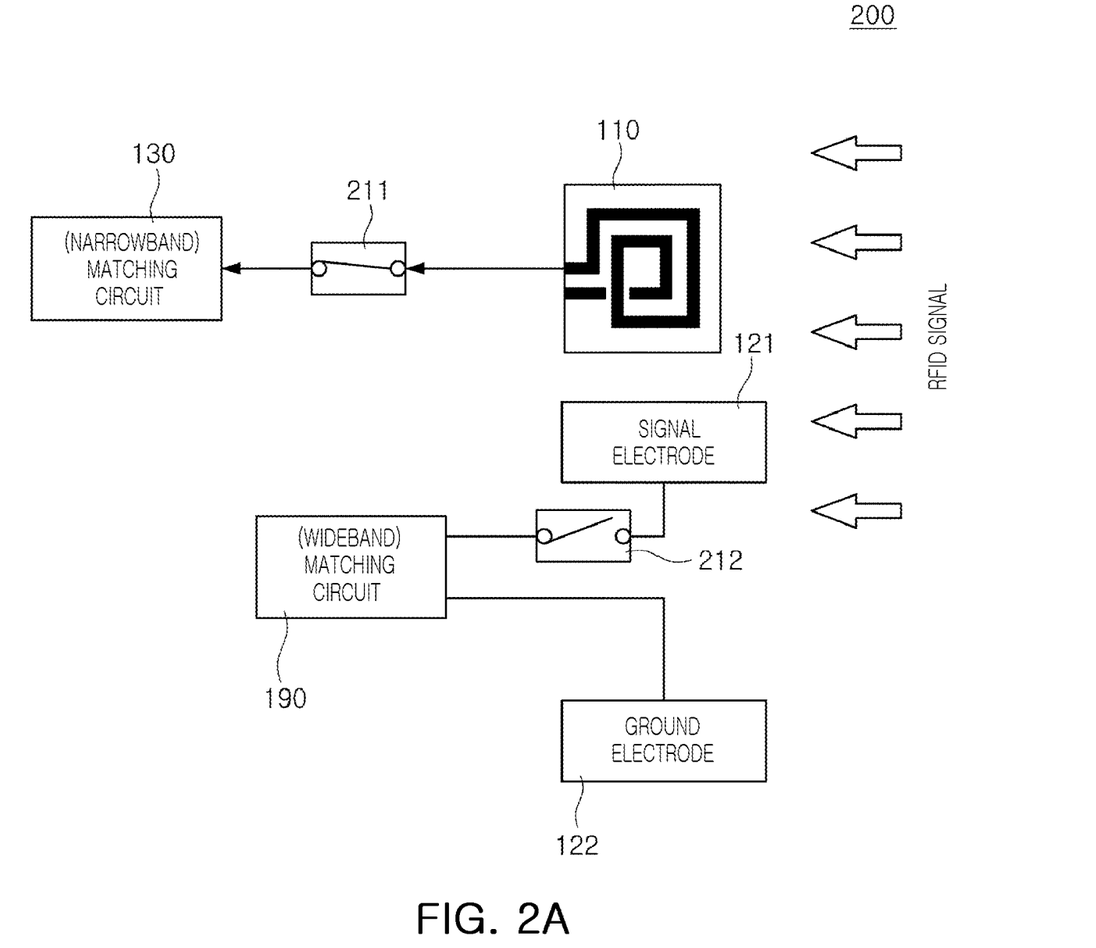
FIGS. 2A to 2B are internal block diagrams of a capsule-type endoscope according to an embodiment of the present disclosure.
Figure 2B:
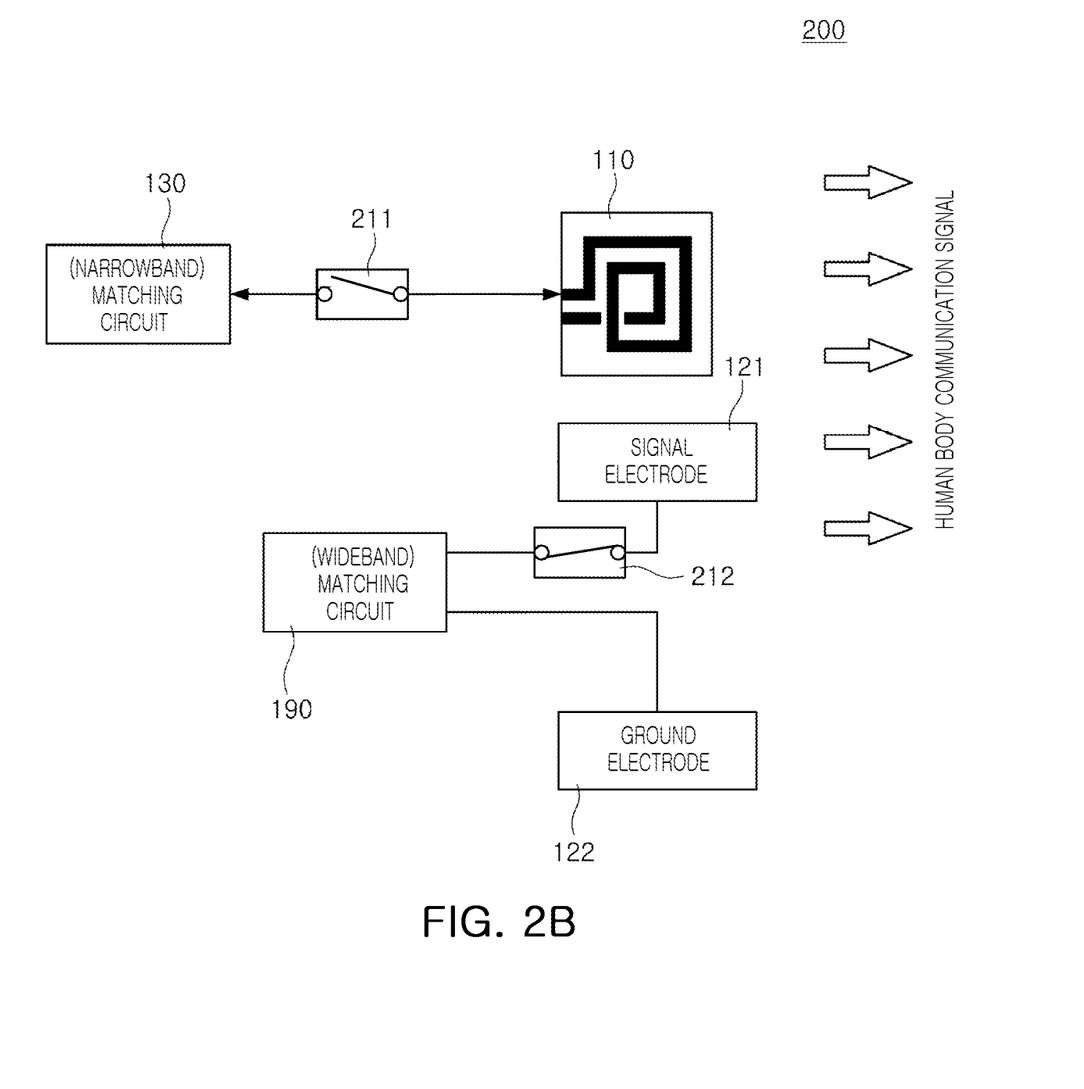

On the other hand, FIGS. 2A and 2B are internal block diagrams of a capsule-type endoscope according to an embodiment of the present disclosure (reference numerals 140 to 180 in FIG. 1 are omitted for convenience), and illustrates that a first switch 211 and a second switch 212 are added to FIG. 1.

FIG. 2A illustrates the opening and closing state of the first switch 211 and the second switch 212 when receiving the RFID signal, FIG. 2B illustrates the open/closed state of the first switch 211 and the second switch 212 when transmitting a signal for human body communication.

As illustrated in FIGS. 2A and 2B, the capsule-type endoscope 300 may further include the first switch 211 for opening and closing the connection between the RFID receiving antenna 110 and the first matching circuit 130, and the second switch 212 for opening and closing the connection between the signal electrode 121 and the second matching circuit 190.

First, as illustrated in FIG. 2A, when receiving the RFID signal, the first switch 211 connects the RFID receiving antenna 110 and the first matching circuit 130, and the second switch 212 may open the connection between the signal electrode 121 and the second matching circuit 190.

In addition, as illustrated in FIG. 2B, when transmitting a signal for human body communication, the first switch 211 opens the connection between the RFID receiving antenna 110 and the first matching circuit 130, and the second switch 212 may connect the signal electrode 121 and the second matching circuit 190.

Figure 3A:
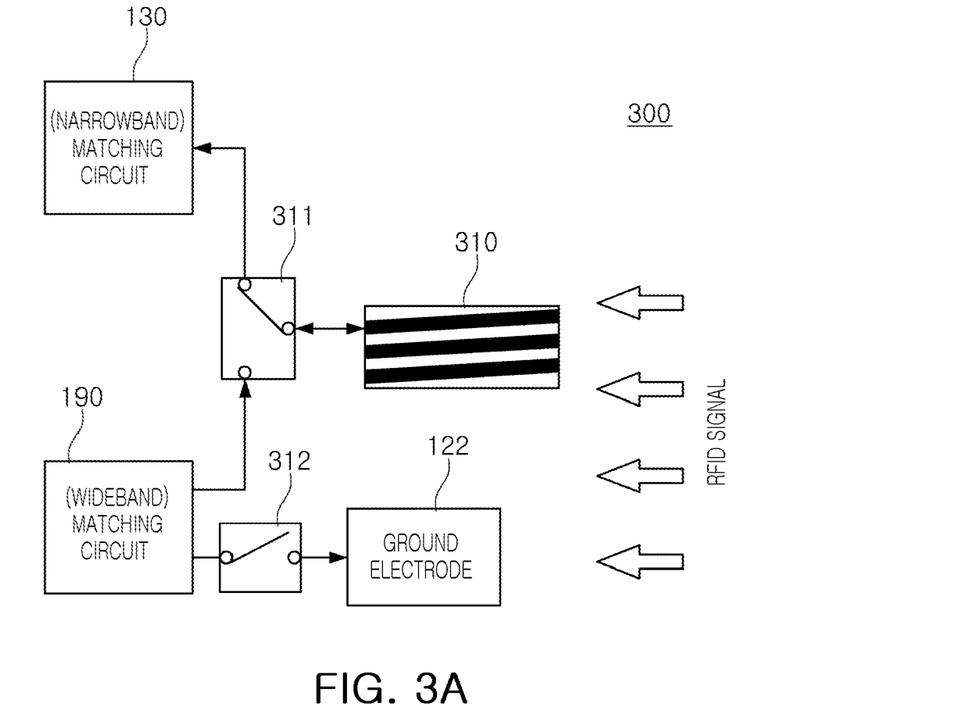
FIGS. 3A to 3B are internal block diagrams of a capsule-type endoscope according to an embodiment of the present disclosure.
Figure 3B:
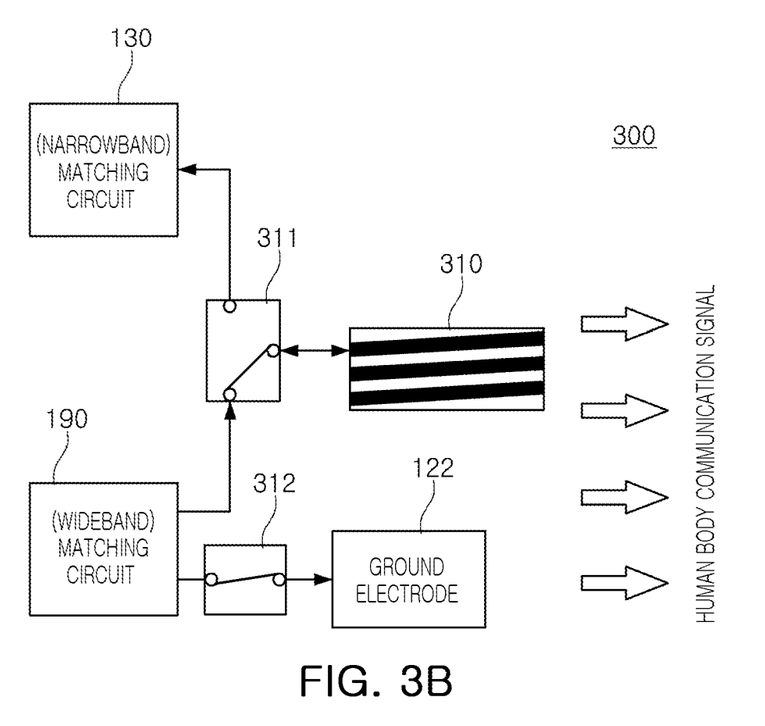

On the other hand, FIGS. 3A and 3B are internal block diagrams of a capsule-type endoscope according to an embodiment of the present disclosure (reference numerals 140 to 180 in FIG. 1 are omitted for convenience), and illustrate that a third switch 311 and a fourth switch 312 are added to FIG. 1, and in this case, the RFID receiving antenna and the signal electrode may be formed as a single integrated electrode 310.

FIG. 3A illustrates the opening and closing state of the third switch 311 and the fourth switch 312 when receiving an RFID signal, and FIG. 3B illustrates an open/closed state of the third switch 311 and the fourth switch 312 when transmitting a signal for human body communication.

As illustrated in FIGS. 3A and 3B, the capsule-type endoscope 300 may further include the third switch 311 selectively connecting the integrated electrode 310 and one of the first matching circuit 130 and the second matching circuit 190, and the fourth switch 312 for opening and closing the connection between the ground electrode 122 and the second matching circuit 190.

First, as illustrated in FIG. 3A, when receiving an RFID signal, the third switch 311 connects the integrated electrode 310 to the first matching circuit 130, and the fourth switch 312 may open the connection between the ground electrode 122 and the second matching circuit 190.

In addition, as illustrated in FIG. 3B, when transmitting a signal for human body communication, the third switch 311 opens the connection between the integrated electrode 310 and the first matching circuit 130, and the fourth switch 312 may connect the ground electrode 122 and the second matching circuit 190.

Figure 4A:
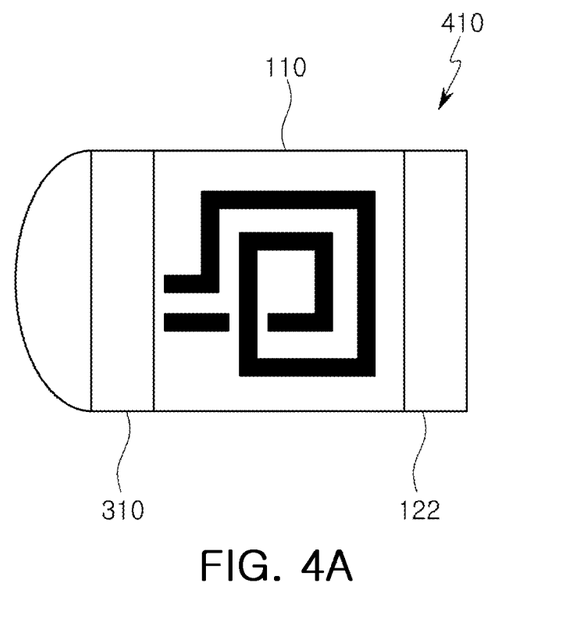
FIGS. 4A to 4B are views illustrating an RFID receiving antenna and a signal electrode of a capsule-type endoscope according to an embodiment of the present disclosure.
Figure 4B:
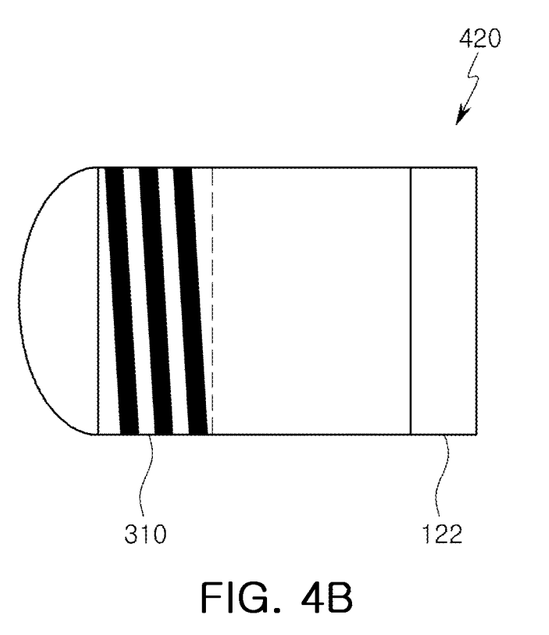

On the other hand, FIGS. 4A to 4B are views illustrating an RFID receiving antenna and a signal electrode of a capsule-type endoscope according to an embodiment of the present disclosure.

As illustrated in FIG. 4A, an RFID receiving antenna 110 may be formed of a material having conductivity, outside of a capsule-type endoscope 410. The RFID receiving antenna 110 may have, for example, a rounded, elliptical, quadrangular loop antenna, meander line antenna, or helical structure. When the RFID receiving antenna 110 is formed outside of the capsule-type endoscope 410, the contact area thereof with the human body may be increased to strength the coupling thereof to a human body communication receiver located outside of the human body, thereby improving communication quality and being advantageous in maintaining a more stable contact point in various environments in the digestive tract.

On the other hand, the RFID receiving antenna 110 may also be formed of a conductive material, inside of the capsule-type endoscope 410. In addition, when the RFID receiving antenna is located inside of the capsule-type endoscope 410, the RFID receiving antenna may be formed of a material having conductivity in a soft material such as an FPCB to be able to be variously modified, and may be formed in a structure integrated with a PCB inserted into a structure or combined after separate manufacturing.

On the other hand, as illustrated in FIG. 4B, the RFID receiving antenna and the signal electrode may also be formed as a single integrated electrode 310 as described above.

As described above, according to an embodiment of the present disclosure, by including an RFID receiving antenna for receiving an RFID signal, a human body communication electrode comprised of a ground electrode and a signal electrode for transmitting a signal for human body communication in a capsule-type endoscope, there is an advantage in that two-way communication may be implemented.

As set forth above, according to an embodiment of the present disclosure, by grafting the RFID tag receiving antenna to the human body communication capsule-type endoscope, a communication channel in which the capsule-type endoscope inside of the human body may be controlled outside of the human body, while not using the power inside of the capsule or using the power inside of the capsule at a minimum, may be configured.

In addition, by combining or integrating the RFID receiving antenna and the human body communication signal electrode, there is an advantage in that the quality of communication may be improved or the configuration may be simplified within a limited structure, and two-way communication may be performed without additional power consumption.

The present disclosure is not limited by the above-described embodiments and the accompanying drawings. It is intended to limit the scope of the rights by the appended claims, and it is possible to substitute, modify, and change in various forms within the scope of the technical spirit of the present disclosure described in the claims, which will be apparent to those of ordinary skill in the art.

What is claimed is:

1. A capsule-type endoscope capable of two-way communication, comprising:
   an RFID receiving antenna receiving an RFID signal;
   a first matching circuit for impedance matching with the RFID receiving antenna;
   a human body communication electrode comprised of a ground electrode and a signal electrode transmitting a signal for human body communication;
   a second matching circuit for impedance matching with the human body communication electrode;
   a first switch for opening and closing a connection between the RFID receiving antenna and the first matching circuit; and
   a second switch opening and closing a connection between the signal electrode of the human body communication electrode and the second matching circuit;
   wherein the first switch connects the RFID receiving antenna and the first matching circuit when the RFID signal is received, and opens a connection between the signal electrode of the human body communication electrodes and the second matching circuit when the human body communication signal is transmitted, and
   the second switch connects the signal electrode of the human body communication electrode and the second matching circuit when the human body communication signal is transmitted, and opens a connection between the RFID receiving antenna and the first matching circuit when the RFID signal is received.

2. The capsule-type endoscope capable of two-way communication of claim 1, wherein the RFID receiving antenna and the signal electrode are provided as a single integrated electrode, and
   the capsule-type endoscope further comprises:
   a third switch selectively connecting the integrated electrode to one of the first matching circuit and the second matching circuit; and
   a fourth switch opening and closing a connection between the ground electrode and the second matching circuit.

3. The capsule-type endoscope capable of two-way communication of claim 1, wherein the RFID receiving antenna is formed of a material having conductivity, outside or inside of the capsule-type endoscope.

4. The capsule-type endoscope capable of two-way communication of claim 1, wherein the RFID receiving antenna has a rounded, elliptical, quadrangular loop antenna, meander line antenna, or helical structure.

5. A capsule-type endoscope capable of two-way communication, comprising:
   an RFID receiving antenna receiving an RFID signal;
   a first matching circuit for impedance matching with the RFID receiving antenna;
   a human body communication electrode comprised of a ground electrode and a signal electrode transmitting a signal for human body communication;
   a second matching circuit for impedance matching with the human body communication electrode,
   wherein the RFID receiving antenna and the signal electrode are provided as a single integrated electrode, and
   the capsule-type endoscope further comprises:
   a third switch selectively connecting the integrated electrode to one of the first matching circuit and the second matching circuit; and
   a fourth switch opening and closing a connection between the ground electrode and the second matching circuit,
   wherein when the RFID signal is received, the third switch connects the integrated electrode to the first matching circuit, and the fourth switch opens the connection between the ground electrode and the second matching circuit; and
   when the human body communication signal is transmitted, the third switch connects the integrated electrode to the second matching circuit, and the fourth switch connects the ground electrode and the second matching circuit.

* * * * *